United States Patent [19]
Friedman

[11] Patent Number: 5,201,655
[45] Date of Patent: Apr. 13, 1993

[54] OPTICAL LIGHT GUIDE FOR CONTROLLING THE IRRADIATION OF A DENTAL RESTORATIVE MATERIAL

[76] Inventor: Joshua Friedman, 13 Fairfield Ct., Ridgefield, Conn. 06877

[21] Appl. No.: 742,179

[22] Filed: Aug. 2, 1991

Related U.S. Application Data

[63] Continuation of Ser. No. 287,867, Dec. 21, 1988, abandoned.

[51] Int. Cl.⁵ .......................... A61C 1/00; A61C 3/00; A61C 5/00
[52] U.S. Cl. ..................... 433/29; 433/215; 385/147
[58] Field of Search .......... 433/29, 215, 229; 350/96.1; 385/147

[56] References Cited

U.S. PATENT DOCUMENTS

| | | | |
|---|---|---|---|
| 1,542,183 | 6/1925 | Steinberg | 350/96.1 |
| 3,590,232 | 6/1971 | Sadowski | 433/29 X |
| 3,683,503 | 8/1972 | Klein | 433/29 |
| 4,445,858 | 5/1984 | Johnson | 433/141 |
| 4,564,355 | 1/1986 | Traiger et al. | 433/215 |
| 4,592,344 | 6/1986 | Scheer | 433/29 X |
| 4,611,992 | 9/1986 | Lokken | 433/29 X |
| 4,666,406 | 5/1987 | Kanca, III | 433/229 |
| 4,673,353 | 6/1987 | Nevin | 433/229 |
| 4,836,782 | 6/1989 | Gonser | 433/215 X |
| 4,867,682 | 9/1989 | Hammesfahr et al. | 433/229 X |
| 4,948,215 | 8/1990 | Friedman | 433/229 X |
| 5,030,093 | 7/1991 | Mitnick | 433/215 X |

FOREIGN PATENT DOCUMENTS

| | | | |
|---|---|---|---|
| 0091876 | 10/1983 | European Pat. Off. | 433/29 |
| 2028994 | 3/1980 | United Kingdom | 433/141 |
| 2196258 | 4/1988 | United Kingdom | 350/96.1 |

*Primary Examiner*—John G. Weiss
*Assistant Examiner*—Nicholas D. Lucchesi

[57] ABSTRACT

A light guide for use in combination with a light source for irradiating a dental restoration. The light guide includes two optical conductors having one end mounted in common for insertion into the light source and with the opposite end of each conductor spaced apart to form a gap into which radiant energy is directly uniformly from opposite sides of the gap.

7 Claims, 1 Drawing Sheet

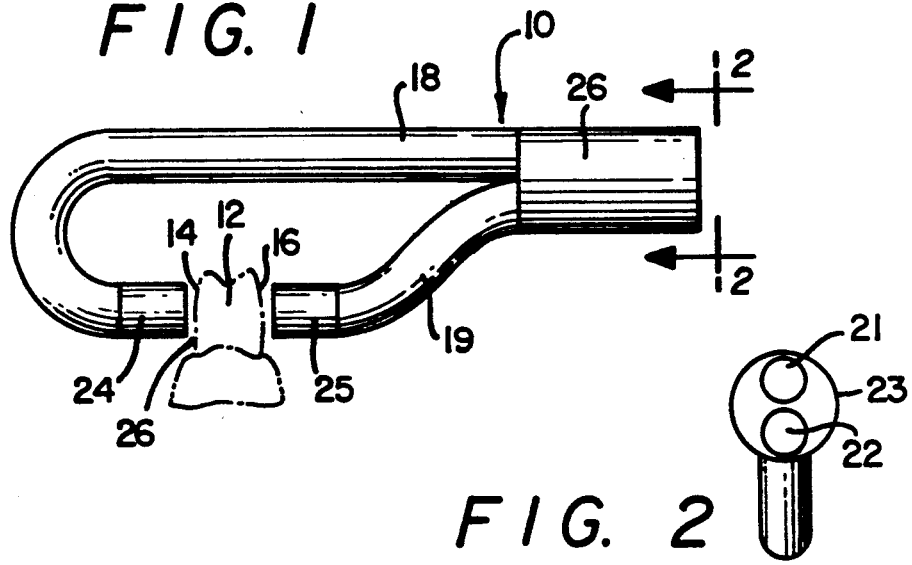
FIG. 1
FIG. 2
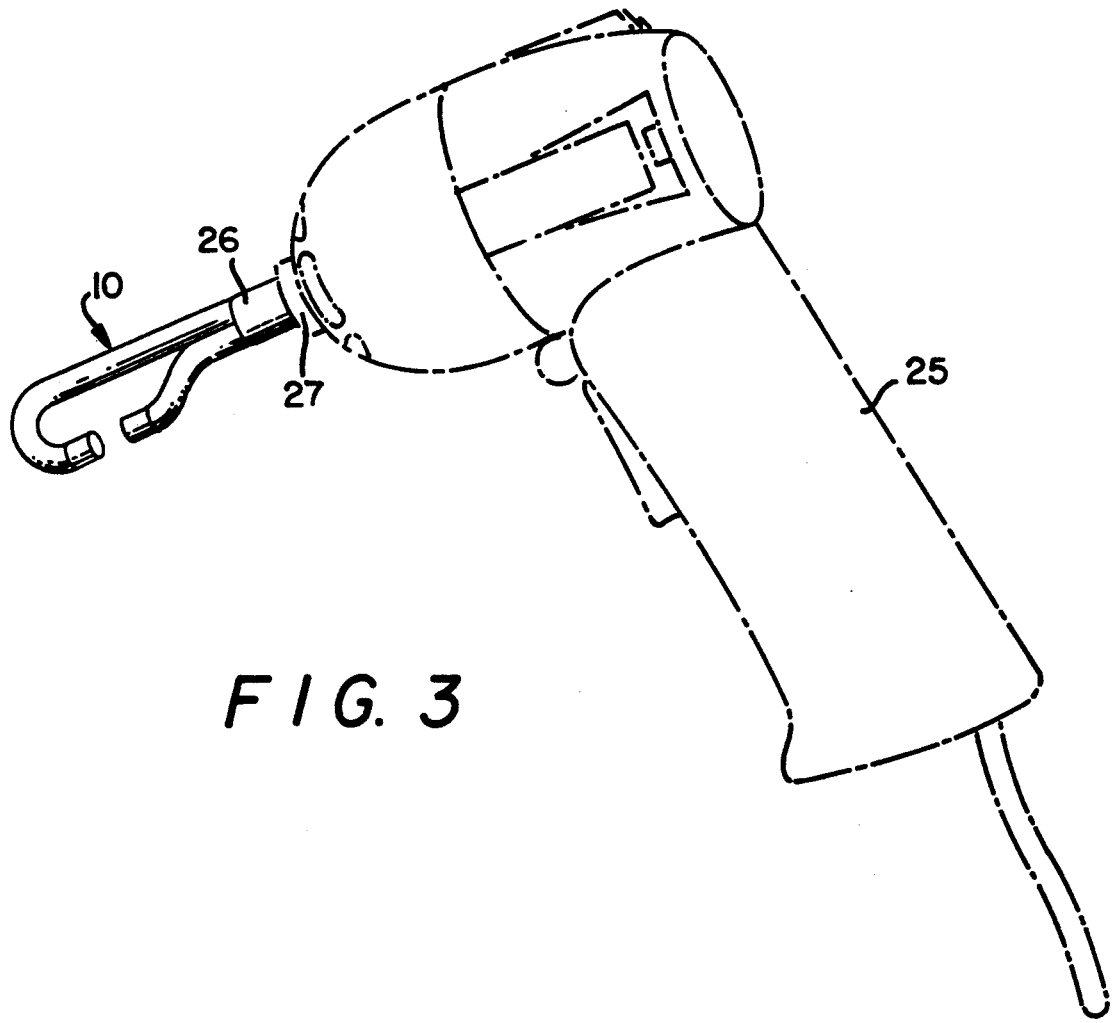
FIG. 3

OPTICAL LIGHT GUIDE FOR CONTROLLING THE IRRADIATION OF A DENTAL RESTORATIVE MATERIAL

This application is a continuation of prior U.S. application Ser. No. 287,867 filed Dec. 21, 1988, now abandoned.

FIELD OF INVENTION

This invention relates to a light guide for use in combination with a light source for controlling the area of irradiation during a dental restorative procedure.

BACKGROUND OF THE INVENTION

The use of photocurable dental materials in the practice of restorative dentistry has become popular. Photocurable materials are cured by exposure to radiant energy in a preselected spectral range in either the ultraviolet or visible spectrum. Presently, such materials are used as a replacement for silver amalgam to fill cavities anteriorly and posteriorly. Photocurable materials are also used to treat prosthetic appliances in the preparation of a dental restoration, such as a crown or bridge, and to repair broken teeth. Some of the advantages of using photocurable compositions include the ease of bonding the material to the tooth structure upon initiating the polymerization irradiation, the ease of color matching and the relatively low solubility of the material. One major disadvantage in the use of a photocurable dental material is shrinkage of the material during polymerization. Shrinkage from polymerization has been determined to progress in the direction of the source of light with the degree of shrinkage being proportional to the distance from the source of energy.

In a typical class II posterior restoration, the gingival floor represents a critical area for providing a good seal between tooth structure and filling material. The gingival floor is highly caries prone because it is located in between the teeth and sometimes subgingival. These conditions make it difficult for proper home cleansing to remove bacterial plaque. Thus, it is extremely important to achieve a good seal at the gingival floor of a restoration and to prevent microleakage which often results in tooth sensitivity and the development of a carious lesion.

In general, the dentist irradiates the photocurable material using a curing light which is directed to the site of the restoration through a light guide such as a fiber optic rod. The light guide is held in a direction so that maximum light energy strikes the occlusal surface, which corresponds to the direction that the restorative filling material is inserted.

SUMMARY OF THE INVENTION

It has been discovered in accordance with the present invention that applying irradiation to the photocurable material uniformly and simultaneously from the labial and lingual sides of the dental restoration instead of the occlusal improves adaptation of the restoration material to the cavity walls. The light guide of the present invention is adapted to be used with a conventional source of light for accomplishing the foregoing and comprises: a short length of an optically conducting member for conducting optical energy from said source of light, and a bifurcated section extending from said member and including at least two arms of optically conducting material with each arm having a distal end spaced apart from each other for directing optical energy uniformly from opposing sides corresponding to the labial and lingual sides of the dental restoration.

Other features, objects and advantages of the present invention will become apparent from the specification and drawings.

DRAWINGS

FIG. 1 is a perspective view of the light guide of the present invention arranged in juxtaposition to a tooth structure to be restored by irradiating the tooth structure from its labial and lingual sides;

FIG. 2 is an end view of the light guide of the present invention taken along the lines 2—2 of FIG. 1; and FIG. 3 shows the light guide of FIG. 1 connected to a conventional hand-held dental curing light source, with the light source shown in phantom.

DETAILED DESCRIPTION OF THE INVENTION

Referring now to FIGS. 1-3 inclusive which show the light guide (10) of the present invention for transmitting radiant energy to a vital tooth structure (12) (shown in phantom) from two opposing sides (14) and (16), representing the labial or buccal and lingual sides of the tooth. The dental procedure may represent filling the tooth with a conventional photocurable dental material which is inserted into the tooth structure (12) through the occlusal surface after removal of decay. The photocurable material may be selected from any commercially available dental composite capable of being polymerized by visible or ultraviolet light including, for example, "Durafill" or "Estilux," trademark products of Kulzer Inc., "Prisma Fill," a trademark product of L.D. Caulk, "Herculite," a trademark product of Kerr Manufacturing Company, "Occlusin," a trademark product of ICI and sold by Coe, "Silux," a trademark product of 3M Company, and Visio-Dispers, a trademark product of ESPE and sold by Priemer.

The light guide (10) includes two fiber optic conductors (18) and (19), each having proximal ends (21) and (22) and distal ends (24) and (25). The proximal ends (21) and (22) are mounted in a common sleeve (23) which is adapted to be inserted into a conventional source of radiant energy such as a halogen lamp. The sleeve 23 contains therein a short length of an optically conducting member which is bifurcated to form the two conductors (18) and (19). The distal ends (24) and (25) are spaced a predetermined distance apart in an opposing relationship and are coaxially aligned. The spacing between the distal ends (24) and (25) forms a gap (26) for positioning the light guide (10) in the mouth of a dental patient, with the distal ends (24) and (25) adjacent the labial (14) and lingual (16) sides of the tooth structure. The spacing may be altered to fit anterior or posterior teeth. The conducting members (18) and (19) may each be a fiber optic rod of glass, quartz or plastic composition.

Although the distal ends (24) and (25) are shown to have a cylindrical configuration, any cross-sectional geometry may be used to more closely conform the distal end to the shape of the tooth.

The proximal ends (21) and (22) are axially aligned in the sleeve casing (23), which is adapted for insertion into a hand-held light gun (25). Any conventional light curing gun (25) or a flexible fiber optic light curing gun (25) or a flexible fiber optic light guide may be used. An adapter (27) may be used to provide a proper fitting to insert the the sleeve into the light source (25). In general, the light source (25) will contain a source of radiant energy (not shown) such as a halogen, mercury vapor, short arc xenon or metal halide lamp, a reflector for directing the radiant energy to a common point adjacent the position of the adapter (27) at the interface with the light guide (10), a filter assembly for filtering light generated from the lamp so as to pass the desired spectral waveband and a control for providing adjustment of power to the lamp.

Optical energy is transmitted from the light source (25) into the light guide (10) which redirects the radiant energy through the optical conductors (18) and (19) to achieve uniform irradiation in the gap (26) from opposite directions through the distal ends (24) and (25) of the light guide (10). The configuration of the conductors (18) and (19) is not critical and is preferably of any shape which is readily insertable into the mouth of a patient to cure the tooth structure (12).

I claim:

1. A light guide for use in combination with a light source for irradiating a single tooth for curing a dental restorative material in such tooth, comprising two fiber optic rods selected from the class consisting of glass, quartz or plastic with each rod having a proximal end joined together to form a common end, means for inserting said common end into said light source, with each optical conductor having a distal end spaced a predetermined distance apart in an opposing coaxially aligned relationship to form a gap adapted to be juxtaposed about opposite sides of said one tooth for directing optical energy of identical wavelength and substantially equal intensity from said light source uniformly into such tooth from such opposite sides, with said opposite sides corresponding to the labial or buccal and lingual sides of said tooth.

2. A light guide, as defined in claim 1, wherein the proximal end of each rod at said common end is mounted in a common sleeve adapted to be removably coupled to said light source.

3. A light guide, as defined in claim 2, wherein said light source is a light-curing gun containing a source of radiant energy selected from the group consisting of a halogen, mercury vapor, short-arc xenon, or metal halide lamp.

4. A light guide, as defined in claim 3, wherein the distal end of each fiber optic rod has a cylindrical cross-sectional geometry.

5. A light guide, as defined in claim 4, wherein each fiber optic rod is composed of a fiber optic rod of glass, quartz or plastic composition.

6. A light guide, as defined in claim 3, wherein the distal end of each fiber optic rod is of a cross-sectional geometry conforming to the shape of the dental restoration.

7. An optical light guide for transmitting radiant energy from a light source into a single tooth to cure a dental restorative material in such tooth comprising a short length of an optically conducting member, means for facilitating insertion of said optically conducting member into said light source for transmitting radiant energy from said light source through said optically conducting member to said single tooth with said optically conducting member being split to form two fiber optic rods selected from the class consisting of glass, quartz, or plastic with each rod having a distal end spaced a predetermined distance apart in an opposing coaxially aligned relationship to form a gap sufficient to fit said one single tooth about opposite sides thereof, so that light of identical wavelength and substantially equal intensity is uniformly directed from such opposite sides into such tooth for curing said dental restorative material.

* * * * *